(12) United States Patent
Brewster et al.

(10) Patent No.: US 7,531,482 B2
(45) Date of Patent: *May 12, 2009

(54) THIENO-PYRIMIDINE COMPOUNDS HAVING FUNGICIDAL ACTIVITY

(75) Inventors: William Kirkland Brewster, Indianapolis, IN (US); David Anthony Demeter, Fishers, IN (US); William Randal Erickson, Carmel, IN (US); Carla Jean Rasmussen Klittich, Zionsville, IN (US); Christian Thomas Lowe, Westfield, IN (US); Brent Jeffrey Rieder, Greenfield, IN (US); Jaime Susanne Nugent, Brownsburg, IN (US); Carla Nanette Yerkes, Crawfordsville, IN (US); Yuanming Zhu, Carmel, IN (US); Terry William Balko, Greenfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 335 days.

This patent is subject to a terminal disclaimer.

(21) Appl. No.: 11/255,448

(22) Filed: Oct. 21, 2005

(65) Prior Publication Data

US 2007/0093498 A1    Apr. 26, 2007

(51) Int. Cl.
C07D 495/04 (2006.01)
A01N 43/90 (2006.01)
(52) U.S. Cl. ...................... 504/241; 544/278
(58) Field of Classification Search ............... 544/278; 504/241
See application file for complete search history.

(56) References Cited

U.S. PATENT DOCUMENTS

| 4,146,716 A | 3/1979 | Cox et al. |
| 4,196,207 A | 4/1980 | Webber et al. |
| 5,141,941 A | 8/1992 | Fujii et al. |
| 5,654,307 A | 8/1997 | Bridges et al. |
| 5,859,020 A * | 1/1999 | Preuss et al. ............... 514/269 |

FOREIGN PATENT DOCUMENTS

| CA | 2038521 | 9/1991 |
| DE | 26 54 090 | 6/1977 |
| EP | 424 125 | 4/1991 |
| EP | 045202 A2 * | 10/1991 |
| EP | 0 447 891 | 4/1994 |
| GB | 2 043 061 | 10/1980 |
| JP | 3063266 | 3/1991 |
| JP | 2762430 | 8/1992 |
| JP | 1995010712 | 1/1995 |

| WO | WO 2004/0912123 A2 * | 10/2004 |

OTHER PUBLICATIONS

Michael Berger, et al; S(+)-4-(1-Phenylethylamino)quinazolines as Inhibitors of Human Immunoglobuline E Synthesis: Potency Is Dictated by Sterochemistry and Atomic Point Charges at N-1; Journal of Medical Chemistry 2001; 44, pp. 3031-3038.
Yoshinori Yamanaka, et al; Quantitative structure-fungicidal activity relationships of N-(4-difluoromethoxybenzyl)-pyrimidin-4-amines against wheat and barley fungi; Pesticide Science, 55:896-902 (1999).

* cited by examiner

Primary Examiner—Brenda L Coleman
Assistant Examiner—Susanna Moore
(74) Attorney, Agent, or Firm—C. W. Arnett

(57) ABSTRACT

The present invention relates to thieno[2,3-d]-pyrimidine compounds having fungicidal activity. Specifically, the present invention relates to compounds having the Formula (I):

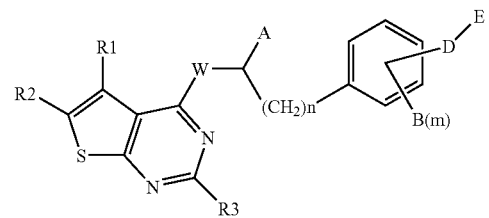

wherein each R1, R2 and R3 is independently selected from the group consisting of H, halogen, and alkyl; A is selected from the group consisting of H and alkyl; W is selected from the group consisting of NH and O; D is selected from O, NH and S; E is (—C(O)—)$_p$—R', wherein p is 0 or 1 and R' is selected from the group consisting of optionally substituted rings selected from phenyl. furanyl, pyridinyl, pyridinyl-N-oxide, pyrimidinyl, pyridazinyl, pyrazinyl, thiazolyl, triazinyl, thiadiazolyl, oxazolyl, isoxazolyl, thienopyrimidinyl, and pyrimidine fused with an aromatic or heteroaromatic ring selected from bejizene, oxazole, isoxazole, furan, thiazole, pyrimidine, pyridine, pyrrole, pyrazine, and thionhene; each ring being ontionally substituted with one or more substituents selected from the group consisting of alkyl, alkenyl, alkynyl, halogen, haloalkyl, alkoxy, haloalkoxy, nitro, cyano, alkylsulfonyl, alkylsulfoxide, alkylthio, alkoxyiminoalkyl, alkylcarbonyl, alkoxycarbonyl, aminocarbonyl, hydroxycarbonyl, phenyicarbonyl, forrnyl, hydrazidocarbonyl, amidoamino, pyrazolyl, triazolonyl, oxadiazolyl, phenyl, nyridinyl, and phenoxyalkyl; B is selected from the group consisting of halogen, alkyl, haloalkyl, and haloalkoxy; n is an integer from 0 to 3; and m is an integer from 0 to 4 with the proviso that when D is O or S and E is phenyl, then E is not further substituted with halogen.

7 Claims, No Drawings

THIENO-PYRIMIDINE COMPOUNDS HAVING FUNGICIDAL ACTIVITY

This invention is related to the field of thieno-pyrimidine compounds having fungicidal activity.

Fungicides are compounds, of natural or synthetic origin, which act to protect plants against damage caused by fungi. However, no one fungicide is useful in all situations. Consequently, research is being conducted to produce fungicides that have better performance, are easier to use, and that cost less.

DE 2,654,090 and U.S. Pat. No. 4,146,716, incorporated herein by reference, disclose thieno-pyrimidine compounds useful for controlling fungal, viral and bacterial plant diseases. U.S. Pat. No. 4,196,207, incorporated herein by reference discloses similar compounds useful in controlling infestations of ticks on animals. CA 2,038,521 and EP-447,891 disclose thieno-pyrimidine derivatives useful as insecticides, growth regulators and herbicides. GB2043061 discloses thienopyrimidine derivatives as plant fungicidal, bactericidal, antiviral, insecticidal and growth regulating compounds. Other references which teach various thieno-pyrimidine compounds for fungicidal use include JP1995010712, JP03063266, EP-424125, and U.S. Pat. No. 5,141,941 (incorporated herein by reference). Pharmaceutical uses of thieno-pyrimidines have also been disclosed in U.S. Pat. No. 5,654,307 (incorporated herein by reference).

However, there remains a need to develop additional thieno-pyrimidine compounds useful as fungicides.

The present invention relates to thieno-pyrimidines, particularly thieno[2,3-d]pyrimidines and their use as fungicides. The compounds of the present invention offer protection against ascomycetes, basidiomycetes, deuteromycetes and oomycetes.

The present invention relates to compounds having the Formula (I):

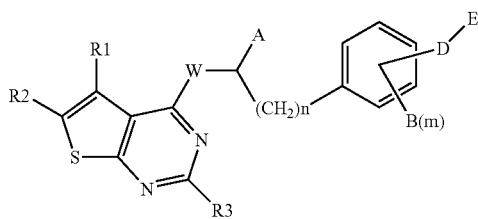

wherein each R1, R2 and R3 is independently selected from the group consisting of H, halogen, and alkyl;
A is selected from the group consisting of H and alkyl;
W is selected from the group consisting of NH and O;
D is selected from O, NH and S;
E is (—C(O)—)p—R', wherein p is 0 or 1 and R' is selected from the group consisting of optionally substituted rings selected from phenyl, furanyl, pyridinyl, pyridinyl-N-oxide, pyrimidinyl, pyridazinyl, pyrazinyl, thiazolyl, triazinyl, thiadiazolyl, oxazolyl, isoxazolyl, thienopyrimidinyl, and pyrimidine fused with an aromatic or heteroaromatic ring selected from benzene, oxazole, isoxazole, furan, thiazole, pyrimidine, pyridine, pyrrole, pyrazine, and thiophene;
each ring being optionally substituted with one or more substituents selected from the group consisting of alkyl, alkenyl, alkynyl, halogen, haloalkyl, alkoxy, haloalkoxy, nitro, cyano, alkylsulfonyl, alkylsulfoxide, alkylthio, alkoxyiminoalkyl, alkylcarbonyl, alkoxycarbonyl, aminocarbonyl, hydroxycarbonyl, phenylcarbonyl, formyl, hydrazidocarbonyl, amidoamino, pyrazolyl, triazolonyl, oxadiazolyl, phenyl, pyridinyl, and phenoxyalkyl;
B is selected from the group consisting of halogen, alkyl, haloalkyl, and haloalkoxy;
n is an integer from 0 to 3; and
m is an integer from 0 to 4
with the proviso that:
when D is O or S and E is phenyl, then E is not further substituted with halogen.

The term "alkyl" refers to an unbranched, or branched, carbon chain having from 1 to 8 carbon atoms ($C_1$-$C_8$ alkyl) unless specified otherwise, including methyl, ethyl, propyl, butyl, isopropyl, isobutyl, tertiary butyl, pentyl, hexyl and the like, preferably from 1 to 6 carbon atoms ($C_1$-$C_6$ alkyl) and most preferably from 1 to 3 carbon atoms ($C_1$-$C_3$ alkyl).

The term "alkenyl", or "alkynyl" refers to an unbranched, or branched, carbon chain having from 3 to 8 carbon atoms, including ethenyl, propenyl, butenyl, isopropenyl, isobutenyl, propynyl, butynyl and the like, preferably from 3 to 6 carbon atoms ($C_3$-$C_6$). As used throughout this specification, the term 'R' refers to the group consisting of $C_{1-8}$ alkyl, $C_{3-8}$ alkenyl or $C_{3-8}$ alkynyl, unless stated otherwise.

The term "alkoxy" refers to an —OR substituent.
The term "alkoxycarbonyl" refers to a —C(=O)—OR substituent.
The term "alkoxyiminoalkyl" refers to a —R=N—O—R substituent.
The term "alkylcarbonyl" refers to a —C(O)—R substituent.
The term "alkylsulfonyl" refers to an —$SO_2$—R substituent.
The term "alkylsulfoxide" refers to an —S(O)—R substituent.
The term "alkylthio" refers to an —S—R substituent.
The term "amidoamino" refers to an —N—N—C(O)R substituent.
The term "aminocarbonyl" refers to —C(O)—$NH_2$ substituent.
The term "cyano" refers to a —C≡N substituent.
The term "formyl" refers to a —CH=O substituent.
The term "haloalkoxy" refers to a —OR—X substituent, wherein R may be substituted with X based on the formula $R=C_nH_{(2n+1)-y}X_y$, wherein X is Cl, F, Br, or I, or any combination thereof and y is an integer from 0 to 2n+1.
The term "haloalkyl" refers to an alkyl, alkenyl or alkynyl substituent which is substituted with Cl, F, I, or Br.
The term "halogen" or "halo" refers to one or more halogen atoms, defined as F, Cl, Br, and I.
The term "hydrazidocarbonyl" refers to —C(O)—N—N—$R_{(2)}$, wherein R is H or $C_1$-$C_3$ alkyl.
The term "hydroxycarbonyl" refers to a —C(O)—OH substituent.
The term "nitro" refers to a —$NO_2$ substituent.
The term "phenoxyalkyl" refers to a —R—O-phenyl substituent.
The term "phenylcarbonyl" refers to an —C(O)-phenyl substituent.

While all the compounds of the present invention have fungicidal activity, certain classes of compounds may be preferred for reasons such as, for example, greater efficacy, reduced toxicity or ease of synthesis.

Throughout the specification, reference to the compounds of Formula I is read as also including optical isomers and salts of Formula I, and hydrates thereof. Specifically, when Y is a branched chain alkyl group, it is understood that such compounds include optical isomers and racemates thereof. Exemplary salts include: hydrochloride, hydrobromide, hydroiodide, and the like.

In one embodiment, the compounds of the present invention are those represented by Formula I wherein:
   R1 is halogen;
   R2 and R3 are each H;
   A is H;
   W is selected from the group consisting of NH and O;
   D is O;
   E is selected from the group consisting of optionally substituted pyridine, pyridine-N-oxide, pyrimidine, thiazole, and thienopyrimidine,
   optionally substituted with one or more groups selected from the group
   consisting of alkyl, haloalkyl, alkoxy, haloalkoxy, alkylsulfonyl, halogen,
   alkylcarbonyl, alkoxycarbonyl, aminocarbonyl, hydroxycarbonyl,
   alkoxycarbonyl, formyl, hydrazidocarbonyl, alkoxyimino, alkoxyiminoalkyl, nitro, and cyano;
   n is 1 and m is 0.

It is also understood by those skilled in the art that additional substitution is allowable, unless otherwise noted, as long as the rules of chemical bonding and strain energy are satisfied and the product still exhibits adequate fungicidal activity.

Another embodiment of the present invention is a use of a compound of Formula I, for protection of a plant against attack by a phytopathogenic organism or the treatment of a plant infested by a phytopathogenic organism, comprising applying a compound of Formula I, or a composition comprising said compound to soil, a plant, a part of a plant, foliage, and/or seeds.

Additionally, another embodiment of the present invention is a composition useful for protecting a plant against attack by a phytopathogenic organism and/or treatment of a plant infested by a phytopathogenic organism comprising a compound of Formula I and a phytologically acceptable carrier material.

The compounds are applied by any of a variety of known techniques, either as the compounds or as formulations comprising the compounds. For example, the compounds may be applied to the roots, seeds or foliage of plants for the control of various fungi, without damaging the commercial value of the plants. The materials are applied in the form of any of the generally used formulation types, for example, as solutions, dusts, wettable powders, flowable concentrates, or emulsifiable concentrates.

Preferably, the compounds of the present invention are applied in the form of a formulation, comprising one or more of the compounds of Formula I with a phytologically acceptable carrier. Concentrated formulations can be dispersed in water, or other liquids, for application, or formulations can be dust-like or granular, which can then be applied without further treatment. The formulations can be prepared according to procedures that are conventional in the agricultural chemical art.

The present invention contemplates all vehicles by which one or more of the compounds can be formulated for delivery and use as a fungicide. Typically, formulations are applied as aqueous suspensions or emulsions. Such suspensions or emulsions are produced from water-soluble, water suspendable, or emulsifiable formulations which are solids, usually known as wettable powders; or liquids, usually known as emulsifiable concentrates, aqueous suspensions, or suspension concentrates. As will be readily appreciated, any material to which these compounds can be added may be used, provided they yield the desired utility without significant interference with the activity of these compounds as antifungal agents.

Wettable powders, which may be compacted to form water dispersible granules, comprise an intimate mixture of one or more of the compounds of Formula I, an inert carrier and surfactants. The concentration of the compound in the wettable powder is usually from about 10 percent to about 90 percent by weight based on the total weight of the wettable powder, more preferably about 25 wt. percent to about 75 wt. percent. In the preparation of wettable powder formulations, the compounds can be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I comprise a convenient concentration, such as from about 10 wt. percent to about 50 wt. percent of the compound, in a suitable liquid, based on the total weight of the concentrate. The compounds are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulfated polyglycol ethers and appropriate salts of phosphated polyglycol ether.

Representative organic liquids which can be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol and the like. Mixtures of two or more organic liquids may also be employed in the preparation of the emulsifiable concentrate. Preferred organic liquids include xylene, and propyl benzene fractions, with xylene being most preferred. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 5 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The compounds of Formula I can also be applied as granular formulations, which are particularly useful for applications to the soil. Granular formulations usually contain from about 0.5 to about 10 wt. percent, bases on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I can be prepared by intimately mixing one or more of the compounds in powdered form with a suitable dusty agricultural carrier, such as, for example, kaolin clay, ground volcanic rock, and the like. Dusts can suitably contain from about 1 to about 10 wt. percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

The formulations may optionally include combinations that contain other pesticidal compounds. Such additional pesticidal compounds may be fungicides, insecticides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I, and the pesticidal compound in the combination can generally be present in a weight ratio of from 1:100 to 100:1.

The compounds of the present invention can also be combined with other fungicides to form fungicidal mixtures and synergistic mixtures thereof. The fungicidal compounds of the present invention are often applied in conjunction with one or more other fungicides to control a wider variety of undesirable diseases. When used in conjunction with other fungicide(s), the presently claimed compounds can be formulated with the other fungicide(s), tank mixed with the other fungicide(s) or applied sequentially with the other fungicide(s). Such other fungicides include 2-(thiocyanatomethylthio)-benzothiazole, 2-phenylphenol, 8-hydroxyquinoline sulfate, antimycin, Ampelomyces, quisqualis, azaconazole, azoxystrobin, Bacillus subtilis, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, Coniothyrium minitans, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M,dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, mandipropamid, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, Reynoutria sachalinensis extract, silthiofam, simeconazole, sodium 2-phenylphenoxide, sodium bicarbonate, sodium pentachlorophenoxide, spiroxamine, sulfur, SYP-Z071, SYP-048, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, tritconazole, validamycin, vinclozolin, zineb, ziram, zoxamide, *Candida oleophila, Fusarium oxysporum, Gliocladium* spp.,

*Phlebiopsis gigantean, Streptomyces griseoviridis, Trichoderma* spp., (RS)-N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithio-carbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, IK-1140, NC-224, and any combinations thereof.

Additionally, the compounds of the present invention can be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present invention are often applied in conjunction with one or more other pesticides to control a wider variety of undesirable pests. When used in conjunction with other pesticides, the presently claimed compounds can be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethyl-amine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as aceto-prole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spiromesifen; thiourea insecticides such as diafenthiuron; urea insecticides such as flucofuron and sulcofuron; and unclassified insecticides such as closantel, crotamiton, EXD, fenazaflor, fenoxacrim, flubendiamide, hydramethylnon, isoprothiolane, malonoben, metaflumizone, metoxadiazone, nifluridide, pyridaben, pyridalyl, rafoxanide, triarathene and triazamate, and any combinations thereof.

Another embodiment of the present invention is a method for the control or prevention of fungal attack. This method comprises applying to the soil, plant, roots, foliage, seed or locus of the fungus, or to a locus in which the infestation is to be prevented (for example applying to cereal or grape plants), a fungicidal effective amount of one or more of the compounds of Formula I. The compounds are suitable for treatment of various plants at fungicidal levels, while exhibiting low phytotoxicity. The compounds are useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

EXAMPLES

The compounds of the present invention are generally prepared by one of two methods.

In the first, the appropriate hydroxyphenylalkylamine A is coupled with a 5-chloro-4-halothieno[2,3-d]pyrimidine B (X=Br, Cl, F, of H) giving intermediates of structure C. These, in turn, are reacted with the appropriate electrophile (E⁺), giving final compounds, D.

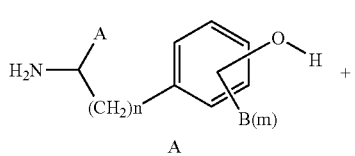

A

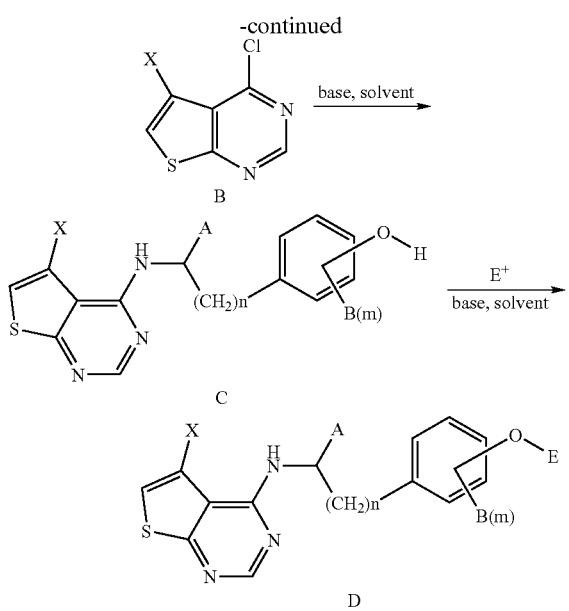

In the second, the appropriate hydroxyphenylalkylamine A (R=H or protecting group) is reacted with the appropriate electrophile (E+), giving intermediates of structure E. These, in turn, are coupled with B (deprotecting first, if necessary)

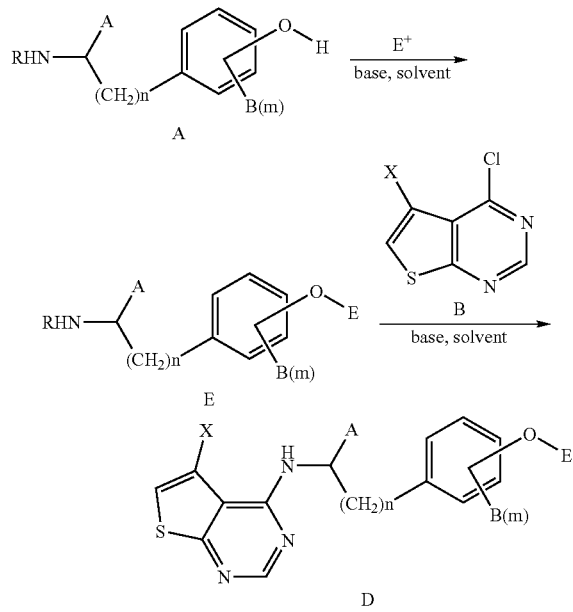

giving the final compounds, D.

In most cases, the first method is the preferred method. If necessary, further elaboration of the distal ring (E) may be performed The coupling steps typically utilize a base in one to four equivalents to facilitate the process and neutralize the acid generated during this step. Examples of bases include, but are not limited to: pyridine, triethylamine, potassium carbonate, and the like. Examples of solvents include, but are not limited to: pyridine, dimethyl formamide (DMF), dimethylsulfoxide (DMSO), ethanol, tetrahydrofuran (THF), dichloromethane and the like. In general, the reaction is carried out at temperatures from about 20 to 150° C. depending upon the method utilized. The intermediates used in this invention are commercially available, known in the literature, or are prepared as described later in this document. The following examples are provided to further illustrate the invention. They are not meant to be construed as limiting the invention.

EXAMPLES

Compound 1

5-(Chlorothieno[2,3-d]pyrimidin-4-yl)-{2-[4-(5-trifluoromethyl pyridin-2-yloxy)phenyl]ethyl}amine A slurry of 4,5-dichlorothieno[2,3-d]pyrimidine (182 mg, (0.89 mmol), 2-[4-(5-trifluoromethylpyridin-2-yloxy)phenyl]ethylamine (250 mg, 0.89 mmol) and triethylamine (5 drops) in DMSO (2 mL) was stirred overnight at room temperature. The reaction was diluted with water (5 mL) and extracted with ethyl acetate (3×25 mL). The organic layers were combined, washed with brine (20 mL) and dried ($Na_2SO_4$). Filtration and removal of solvent left a residue that was chromatographed on silica gel eluting with 4:1 methylene chloride/ethyl acetate. Product fractions were combined and stripped leaving 164 mg of an impure off-white solid. Recrystallization from cyclohexane afforded pure product as a white powder, 116 mg, 0.26 mmol, 29 percent yield.

Compounds 2, 3, 4, 5, 6 were prepared similarly according to the procedures for Example 1, using amine salts described later.

Compound 7

{2-[4-(5-Bromopyridin-2-yloxy)phenyl]ethyl}-(5-chlorothieno[2,3-d]pyrimidin-4-yl}amine A solution of 4-{2-[(5-chlorothieno[2,3-d]pyrimidin-4-yl)amino]ethyl}phenol (200 mg, 0.65 mmol), 2-fluoro-5-bromopyridine (115 mg, 0.65 mmol) and potassium carbonate (90 mg, 0.65 mmol) in DMSO (2 mL) was stirred over night at 75° C. The mixture was diluted with $H_2O$ (15 mL). This mixture was extracted with $Et_2O$ (3×15 mL). The organics were combined, washed with brine, dried ($Na_2SO_4$) and filtered through silica gel. The solvent was stripped and the residue triturated with ether leaving a yellow solid, 191 mg, 0.62 mmol, 95 percent yield.

Compounds 8, 9, 10, 12, 13, 16, 17, 18, 19, 20, 21, 23, 24, 26, 27, 28, 29, 30, 31, 32, 35, 36, 37, 38, 39, 40, 41, 43, 44, 45, 46, 51, 56, 57, 58, 59, 60, 66, 72, 73, 79, 80, 82, 83, 84, 85, 89, 90, 91, 92, 93, 95, 96, 97, 98, 100, 101, 106, 125, 128, 129, 130, 131, 132, 133 were prepared similarly using the procedure of Compound 7.

Compounds 71, 74, 75, 76, 77 were prepared according to the procedure of Compound 7 substituting DMF for DMSO:

Compounds 42, 49, 50, 78, 81 were prepared according to the procedure of Compound 7, substituting sodium hydride for potassium carbonate:

Compounds 47, 53, 55, 61, 62 were prepared according to the procedure of Compound 7, substituting triethylamine and DMF for potassium carbonate and DMSO:

Compounds 52, 54, 63, 64, 65, 68, 70, 86, 87, 88, 103, 111, 126 were prepared according to the procedure of Compound 7, substituting sodium hydride and DMF for potassium carbonate and DMSO:

Compounds 94, 109, 110, 112, 114, 115, 116, 117, 118, 119, 120, 121, 122, 123 were prepared according to the procedure of Compound 7, substituting potassium t-butoxide and THF for potassium carbonate and DMSO:

Compound 108 was prepared according to the procedure of Compound 7, substituting pyridine and methylene chloride for potassium carbonate and DMSO:

Compound 113 was prepared according to the procedure of Compound 7, substituting sodium methoxide and methanol for potassium carbonate and DMSO:

Compound 11

4-Methoxybenzoic acid 4-[2-(5-Chlorothieno[2,3-d]pyrimidin-4-ylamino)ethyl]phenyl ester A solution of 6-methoxynicotinoyl chloride (343 mg, 2 mmol) in $CH_2Cl_2$ (5 mL) was added dropwise to a solution of 4-{2-[(5-chlorothieno[2,3-d]pyrimidin-4-yl)amino]ethyl}phenol (611 mg, 2 mmol) and $Et_3N$ (1.0g, 10 mmol) in $CH_2Cl_2$ (5 mL) and the solution was stirred at room temperature overnight. The reaction was diluted with $CH_2Cl_2$ (20 mL) and washed with $H_2O$, 1M NaOH, and brine. The organics were dried ($Na_2SO_4$) and filtered through silica gel. The solvent was stripped yielding 200 mg of material which was purified via HPLC giving 48mg, 0.11 mmol, 5 percent yield.

Compounds 14, 15, 25 were prepared similarly using to the procedure of Compound 11

Compound 33

6-{4-[2-(5-Chlorothieno[2,3-d]pyrimidin-4-ylamino)ethyl]phenoxy}nicotinic acid N',N'-dimethylhydrazide A solution of 6-{4-[2-(5-Chlorothieno[2,3-d]pyrimidin-4-ylamino)ethyl]phenoxy}nicotinic acid (0.5 g, 1.1 mmol) in thionyl chloride (15 mL) was heated at reflux for 1 hour, then cooled and concentrated in vacuo. The residue was taken up in methylene chloride (20 mL) and treated with N,N-dimethylhydrazine. After 1 h, the reaction was washed with water (20 mL) and dried ($Na_2SO_4$). Filtration and removal of solvent left a residue which was recrystallized from ethyl acetate, 0.18 g, 0.44 mol, 35 percent yield.

Compound 34

6-{4-[2-(5-Chlorothieno[2,3-d]pyrimidin-4-ylamino)ethyl]phenoxy}pyridine-3-carbaldehyde O-methyloxime A solution of 6-{4-[2-(5-Chlorothieno[2,3-d]pyrimidin-4-ylamino)ethyl]phenoxy}pyridine-3-carbaldehyde (0.2 g, 0.5 mmol) and methoxylamine hydrochloride (0.2 g, 2.5 mmol) in ethanol (10 mL) was heated at reflux for 1 hour. After cooling, the reaction was diluted with water and the solid collected by filtration and air dried affording product, 0.17 g, 0.4 mmol, 77 percent yield.

Compound 48

1-2-{4-[2-(5-Chlorothieno[2,3-d]pyrimidin-4-ylamino)ethyl]phenoxy}thiazole-5-yl)ethanone O-methoxime A solution of the ketone 46 (258 mg, 0.6 mmol), methoxylamine hydrochloride (50 mg, 0.6 mmol), and sodium acetate (60 mg, 0.7 mmol) in dioxane (2 mL) was heated at 50° C. overnight. After cooling, the reaction was diluted with ether and washed with water, brine, and dried ($Na_2SO_4$). This was filtered through a small pad of silica gel, eluting with ether until product was collected, leaving product, 55 mg, 0.12 mmol, 20 percent yield.

Compound 67

(5-Chlorothieno[2,3-d]pyrimidin-4-yl)-{2-[3-(5-trifluoromethylpyridin-2-yloxy)phenyl]ethyl}amine To a Carousel reactor tube equipped with a magnetic stirrer under an atmosphere of nitrogen was added DMF (5 mL), 3-[2-(5-chlorothieno[2,3-d]-pyrimidin-4-ylamino) ethyl]phenol (678 mg, 2.2 mmol), and sodium hydride (60 percent dispersion in oil; 98 mg). After bubbling subsided to yield a brown solution, 2-fluoro-5-trifluoromethylpyridine (366 mg, 2.2 mmol) then was added. The reaction was stirred at 40° C. for 15 h. Then the reaction mixture was partitioned between water (10 mL) and ethyl acetate (3×20 mL). The combined organic phases were diluted with pentane (15 mL), washed sequentially with water (2×10 mL) and brine (10 mL), then dried ($MgSO_4$) and filtered through a silica gel/Celite plug. Most of the solvent was removed to give thick yellow oil (1.05 g), which was vigorously stirred with pentane (50 mL). The pentane was decanted to leave a tan solid. The solid was triturated in hot pentane, the suspension was cooled, and the solid removed by suction filtration to give product as an amorphous tan powder, 545 mg, 1.2 mmol, 55 percent yield, mp 67-69° C.

Compound 69 was prepared similarly using the procedure of Compound 67.

Compound 84

(5-Chlorothieno[2,3-d]pyrimidin-4-yl)-{2-[4-(6-methoxypyridin-2-yloxy)phenyl]ethyl}amine A solution of 19 (0.34 g, 0.85 mmol) in methanol (10 mL) was treated with ethyl chloroformate (0.11 g, 0.11 mmol) followed by triethylamine (0.24 mL, 1.71 mmol). The mixture was heated at reflux for 4h, then additional ethyl chloroformate (0.11 g, 0.11 mmol) and triethylamine (0.24 mL, 1.71 mmol) were added. After stirring for 3 days at 38° C., the solvent was removed in vacuo and the residue dissolved in chloroform. The organic layer was washed with 1:1 solution of sat'd. aq. sodium bicarbonate and brine and dried ($Na_2SO_4$). Filtration and removal of solvent left a residue which was purified on silica gel eluting with 25 percent acetone in hexanes, affording product as a colorless oil, 89 mg, 0.22 mmol, 25 percent yield.

Compound 99

2-Chloro-N-{4-[2-(5-chlorothieno[2,3,-d]pyrimidin-4-ylamino)ethyl]phenyl}isonicotinamide 2-chloroisonicotinoyl chloride (0.1 g, 0.57 mmol) was added to a solution of 2-[(4-aminophenyl)ethyl]-(5-chlorothieno[2,3,-d]pyrimidin-4-yl)amine (0.15 g, 0.50 mmol) in methylene chloride (20 mL) resulting in a beige precipitate. Pyridine (0.05 g) was added and the resultant solution stirred for 15 minutes. The solvents were removed in vacuo and the residue partitioned between water and ethyl acetate. The layers ere separated and the organic layer concentrated in vacuo. This residue (0.26 g) was taken up in minimal methylene chloride and precipitated by the addition of hexanes. The product was collected by filtration and air dried affording a tan powder, 0.15 g, 0.33 mmol, 66 percent yield.

Compound 102

2,2-Dimethylpropionic acid N'-(6-{4-[2-(5-chlorothieno[2,3-d]pyrimidin-4-ylamino)ethyl]phenoxy}pyridine-2-yl)-hydrazide To a solution of 4-{2-[(5-chlorothieno[2,3-d]pyrimidin-4-yl)amino]ethyl}phenol (0.152 g, 0.5 mmol) and 5-(tert-butyl)-3-(6-fluoropyridin-2-yl)-3H-[1,3,4]oxadiazol-2-one (0.119 g, 0.5 mmol) in anhydrous DMF (4 mL) was added 60 percent sodium hydride in mineral oil (30 mg, 0.75 mmol) portionwise. The mixture was then stirred at 100° C. overnight. After cooling the reaction was quenched with methanol. The solvent was removed in vacuo and the residue was triturated in $CH_2Cl_2$ and water. The organic phase was separated, dried over anhydrous $Na_2SO_4$, filtered, concentrated, and purified on preparative HPLC to give the decarboxylated product as a brownish foam, 16 mg, 0.03 mmol, 6.5 percent yield.

Compound 104

{2-[4-(6-Chloropyridin-3-ylmethoxy)phenyl]ethyl-(5-chlorothieno[2,3, -d]pyrimidin-4-yl)amine To a solution of NaH 60 percent (65 mg, 1.6 mmol) in DMSO (2 mL) was added 4-{2-[(5-chlorothieno[2,3-d]pyrimidin-4-yl)amino]ethyl}phenol (305 mg, 1 mmol). The solution was stirred for 30 min, and then a solution of 2-chloro-5-(chloromethyl)pyridine (162 mg, 1 mmol) in DMSO (2 mL) was added. The solution was stirred overnight while heating to 50° C. The reaction was diluted with $H_2O$ and extracted thrice with ether. The organics were washed with brine and dried ($Na_2SO_4$). Filtration and removal of solvent left a yellow solid that was purified by chromatography on silica eluting with 40 percent ethyl acetate in pentane affording a white solid, 210 mg, 0.55 mmol, 55 percent yield.

Compounds 105, 107 were prepared similarly using the procedure of Compound 104.

Compound 124

(5-Chlorothieno[2,3-d]pyrimidin-4-yl)-{2-[3-methoxy-4-(4-trifluoromethylpyridin-2-yloxy)phenyl]ethyl}amine To a solution of 60 percent sodium hydride / oil dispersion (31 mg, 0.78 mmol) in DMSO (3 mL) was added 4-{2-[(5-chlorothieno[2,3-d]pyrimidin-4-yl)amino]ethyl}-2-methoxyphenol (250 mg, 0.75 mmol). After stirring for 30 min, 2-chloro-4-(trifluoromethyl)pyridine (141 mg, 0.78 mmol) was added and the reaction heated at 80° C. overnight. The reaction mixture was diluted with $H_2O$ and the precipitate collected by filtration. The filter cake washed with $H_2O$ and then dissolved in $CH_2Cl_2$. The organics were dried with ($Na_2SO_4$), filtered and the stripped in vacuo. The solid residue was triturated with a mixture of ether and pentane leaving a brown solid, 120 mg, 0.25 mmol, 33 percent yield.

Compound 127

(5-Chlorothieno[2,3-d]pyrimidin-4-yl)-(2-{4-(2,2,2-trifluoroethoxy)pyridin-2-yloxy)phenyl}ethyl)amine A 45 mL Parr vessel was charged with compound 43 (200 mg, 0.39 mmol), cesium carbonate (253 mg, 0.78 mmol), 1,10-phenanthroline (14 mg, 0.078 mmol), copper(I) iodide (7 mg, 0.039 mmol) and 2,2,2-trifluoroethanol (4 mL, 0.78 mmol). The reaction was heated to 110° C. for 72 hours. The reaction was cooled to ambient temperature, diluted with $Et_2O$ and washed with $H_2O$. The organics were dried ($Na_2SO_4$), filtered, and the solvent was removed in vacuo. The residue was chromatographed on silica eluting with 30 percent EtOAc in pet ether, leaving product as a colorless oil, 58 mg, 0.12 mmol, 30 percent yield.

Syntheses of Miscellaneous Intermediates

Preparation of 4-[2-(5-Chlorothieno[2,3-d]pyrimidin-4-ylamino)ethyl]phenol

A mixture of 4,5-dichlorothieno[2,3-d]pyrimidine (0.5 g, 2.4 mmol), tyramine (0.4 g, 2.9 mmol) and triethylamine (0.4 g, 3.6 g, mmol) in DMF (5 mL) was stirred overnight at room temperature. The reaction was partitioned between water (25 mL) and ethyl acetate (25 mL) and the layers separated. The aqueous portion was extracted with additional ethyl acetate (2×25 mL) and the organic layers were combined, washed with water (2×20 mL), brine (25 mL) and dried ($Na_2SO_4$). Filtration and removal of solvent afforded 0.5 g of a brown solid. This was purified by chromatography on silica eluting with 40 percent ethyl acetate / hexanes giving product as a pale yellow solid, 310 mg, 1.0 mmol, 42 percent yield.

The following compounds were prepared according to the above procedure: 4-[2-(5-Bromothieno[2,3-d]pyrimidin-4-ylamino)ethyl]phenol. 4-[2-(Thieno[2,3-d]pyrimidin-4-ylamino)ethyl]phenol.

Preparation of 3-[2-(5-chlorothieno[2.3-d]pyrimidin-4-ylamino)ethyl]phenol

Into a 250-mL, 3-necked, round-bottom flask, equipped with a mechanical stirrer, condenser, dropping funnel, and thermocouple temp monitor, under an atmosphere of nitrogen was added N,N-dimethylformamide (75 mL) , 4,5-dichlorothieno[2,3-d]pyrimidine (7.47 g, 36 mmol), 3-hydroxyphenethylamine hydrochloride (5.0 g, 28.8 mmol), and triethylamine (10.7 mmol). After exothermic mixing of the reagents raised the temperature of the reaction mixture to 33° C., the mixture was allowed to stir overnight while returning to 25° C. Then the mixture was poured into water and extracted with warm (60° C.) ethyl acetate (5×70 mL). The combined organic phases were washed with water (2×70 mL), brine (70 mL), dried ($MgSO_4$), filtered through silica gel/Celite plug, and most of the solvent removed in vacuo to give a yellow oil. The oil was dissolved in ethyl acetate (100 mL), heated to reflux, and allowed to cool to 25° C. A yellow crystalline solid formed, and was removed via suction filtration; the product was air dried on the funnel for 3 h, to give 6.34 g, 20.8 mmol, 72 percent yield, 164-165° C.

Preparation of 2-[(4-Aminophenyl)ethyl]-(5-chlorothieno[2,3,-d]pyrimidin-4-yl)amine A mixture of 4,5-dichlorothieno[2,3-d]pyrimidine (0.62 g, 3 mmol), 4-aminophenethylamine (0.41 g, 3 mmol) and potassium carbonate (2 g, 14 mmol) in THF (60 mL) was heated at 100° C. for 15 minutes. After cooling, the solids were removed by filtration and the mother liquor reduced to dryness. The residue was taken up in 1:1 solution of ethyl acetate and ether and washed with dilute aqueous sodium hydroxide. The organic phase was then extracted twice with dilute aqueous hydrochloric acid solution, and the combined aqueous portions washed with ether. The pH of the aqueous phase was raised to 9 with sodium hydroxide, then extracted exhaustively with ether. This organic phase was filtered to remove some insoluble material leaving a clear yellow solution. Removal of solvent afforded product as a yellow powder, 580 mg, 1.9 mmol, 63 percent yield.

Preparation of 4-[2-(5-Chlorothieno[2,3-d]pyrimidin-4-ylamino)ethyl]-2-methoxyphenol A solution of 4,5-dichlorothieno[2,3-d]pyrimidine (2.0 g, 9.8 mmol), 4-(2-aminoethyl)-2-methoxyphenol (1.8 g, 10.7 mmol) and triethylamine (1.2 g, 11.8 mmol) in DMF (15 mL) was stirred overnight. The solution was diluted with $H_2O$ and the product collected by filtration yielding an off white powder, 2.5 g, 7.4 mmol, 76 percent yield.

Preparation of 2-[4-(5-Trifluoromethylpyridin-2-yloxy)phenyl]ethylamine

Sodium hydride/60 percent oil dispersion (0.72 mg, 18 mmol) was added in portions to a slurry of tyramine (2.1 g, 15 mmol) in anh. DMF (25 mL). After 15 minutes, 2-chloro-5-(trifluoromethyl)pyridine (2.9 g, 16 mmol) was added neat and the reaction heated to 50° C. for 3 hours. After cooling, the reaction was poured into water (100 mL) and extracted with ethyl acetate (3×50 mL). The organic portions were combined and washed with brine (50 mL) and dried ($Na_2SO_4$). Filtration and removal of solvent left a brown residue that partially solidified. This was triturated in minimal ethyl acetate and collected by filtration, leaving product as a white solid, 3.0 g, 10.6 mmol, 71 percent yield.

Preparation of 2-[4-(5-Methanesulfonylpyridin-2-yloxy)phenyl]ethylamine

Sodium hydride/60 percent oil dispersion (202 mg, 5.0 mmol) was added in portions to a 5° C. slurry of N-boc protected tyramine (1.0 g, 4.2 mmol) in anh. THF (8 mL). Stirring was continued for 30 minutes while allowing the reaction to warm to room temperature. 2-Chloro-5-methanesulfonylpyridine (843 mg, 4.4 mmol) was added and the resultant slurry stirred overnight. Water (50 mL) was added, the majority of THF removed in vacuo and the residue was extracted with methylene chloride (3×50 mL). The organics were combined, washed with brine (50 mL) and dried ($Na_2SO_4$). Filtration and removal of solvent left an off-white powder, 1.7 g, 4.3 mmol. TLC (1:1 hexanes/ethyl acetate) indicate trace impurities are present, but the crude N-boc material used as is in the next step.

Trifluoroacetic acid (1.5 mL, 20 mmol) was added to a slurry of the above crude N-boc protected amine (785 mg, 4.2 mmol) in methylene chloride (12 mL). The resultant solution was stirred for 4 hours, then the solvent and excess reagent were removed under a nitrogen stream, leaving the trifluoroacetic acid salt of the desired amine, which was used immediately in the coupling step.

The following compounds were made according to the above procedure:

2-[4-(5-Nitropyridin-2-yloxy)phenyl]ethylamine, trifluoroacetic acid salt.

2-[4-(5-Cyanopyridin-2-yloxy)phenyl]ethylamine, trifluoroacetic acid salt.

2-(4-Thiazol-2-yl-phenyl)ethylamine, trifluoroacetic acid salt.

Preparation of 4-[4-(2-Aminoethyl phenoxy]benzoic acid, tert-butyl ester

Tyramine (700 mg, 5.1 mmol) was added to a magnetically stirred suspension of potassium hydride (35 wt. percent dispersion in oil; 876 mg, 7.64 mmol) in DMF (20 mL) at 25° C. After effervescence stopped, tert-butyl 4-fluorobenzoate (1.0 g, 5.1 mmol) was added. After stirring at 25° C. for 64 hours, the reaction was warmed to 60° C. After 48 h, the reaction was poured into brine and extracted with hexanes (3×25 mL) and ethyl acetate (2×25 mL). Organic layers washed separately with aqueous 2 N NaOH, dried ($Na_2SO_4$), then pooled, evaporated and purified by silica gel chromatography ($CH_2Cl_2$:MeOH/2:1) to provide 0.98 g of clear oil.

Preparation of 5-(4-Pyridyl)-2-chloro-1,3,4-thiadiazole t-Butyl nitrite (3.3 mL, 42 mmol) was added to a solution of 5-(4-pyridyl)-2-amino-1,3,4-thiadiazole (5.0 g, 28 mmol) and copper (I) chloride (3.8 g, 34 mmol) in acetonitrile (100 mL) and the reaction stirred for five days. Ether and dilute aqueous sodium hydroxide were added and stirred for 15 minutes. The liquids were decanted from the solid material and the gelatinous solid triturated twice more with ether. All the liquids were combined, and the aqueous phase separated. The organic phase was washed with brine and dried ($Na_2SO_4$). Filtration and removal of solvent left product as a tan solid, 2.4 g, 12 mmol, 43 percent yield.

Preparation of 1-(2-Chlorothiazol-5-yl)ethanone

A solution of 2-chlorothiazole (2.5 g, 21 mmol) in THF (10 mL) was added dropwise to a chilled (−75° C.) 2.5 M hexanes solution of n-BuLi (9.2 mL, 23 mmol) in THF (70 mL). After the addition was complete the reaction mixture was stirred for 1 hr. Then a solution of N-methoxy-N-methylacetamide (2.4 g, 23 mmol) in THF (5 mL) was added. The reaction was allowed to stir overnight while warming to 25° C. The reaction was diluted with $H_2O$ and thrice extracted with ethyl ether. The organic portions were combined, washed with brine and then dried ($Na_2SO_4$). Filtration and removal of solvent gave a residue that was purified by flash chromatography on silica eluting with 5 percent $Et_2O$ in pentane, affording product as a white solid, 2.5 g, 15.5 mmol, 73 percent yield.

Preparation of 2-Chloro-4-(2,2,2-trifluoroethoxy)pyrimidine

To a suspension of sodium hydride/60 percent oil dispersion (286 mg, 7.1 mmol) in DMF (10 mL) was added 2,2,2-trifluoroethanol (675 mg, 6.7 mmol). The reaction mixture was stirred for 30 minutes, then it was then added dropwise over 30 minutes to a solution of 2,4-dichloropyrimidine (1.0 g, 6.7 mmol). The solution was then allowed to stir overnight while warming to room temperature. The solution was diluted with $H_2O$ and extracted thrice with $Et_2O$. The organics were combined, washed with brine, dried ($Na_2SO_4$) and filtered through silica gel, eluting with ether. The product was isolated as a semi-solid, 1.1 g, 5.2 mmol, 78 percent yield.

Preparation of 4-Bromomethyl-5-isopropylprimidine

4-Methyl-6-isopropylpyrimidine (3.0 g, 22 mmol) was dissolved in 30 ml dichloromethane, cooled in ice-salt and treated dropwise with bromine (3.8 g, 24 mmol) over 20 m. One hour after stirring at 0-10° C. the mixture was treated with a dilute aqueous sodium bisulfite. The organic phase was separated, washed with water, dried over sodium sulfate and evaporated. The unstable bromo compound (ca. 85 percent pure) was used directly for coupling.

Preparation of 4-Methyl-6-isopropylpyrimidine

4-Chloro-5-isopropyl-6-methylpyrimidine (5.0 g, 29 mmol) and sodium acetate (3.1 g, 38 mmol) were combined in 75 ml methanol and hydrogenated over 500 mg 5 percent palladium on carbon for 20 h. After removal of the catalyst by filtration, the solvent was removed by evaporation. The residue was treated with sat. sodium bicarbonate solution and extracted with diethyl ether. The ether extracts were washed with sat. brine, dried ($Na_2SO_4$) and evaporated to give 3.2 g (81 percent yield).

Preparation of 4-Chloro-5-isopropyl-6-methylpyrimidine

4-Hydroxy-5-isopropyl-6-methylpyrimidine (12.2 g, 80 mmol) was added to 50 ml phosphorous oxychloride and treated with ca. 0.1 ml DMF. The mixture was heated to 60-70° C. and stirred for 2h. After cooling the excess $POCl_3$ was removed under vacuum, the residue was poured onto ice and the pH of the aqueous layer was adjusted to 7 by addition of NaOH and $NaHCO_3$. The product was taken up in dichloromethane, washed with sat. sodium bicarbonate, dried ($Na_2SO_4$) and evaporated. The residue was purified by vacuum distillation to yield 8.5 g (62 percent yield).

Preparation of 4-Hydroxy-5-isopropyl-6-methylpyrimidine 550 ml of 12 percent hydrogen peroxide solution was heated to 60° C. 4-Hydroxy-5-isopropyl-6-methylpyrimidine-2-thiol (50 g, 0.27 mole) was added in portions. The temperature was maintained at 70-75° C. by rate of addition and application of external heat. 20 min. after completion of the addition approx. 150 ml of distillate was removed under vacuum. The pH was adjusted to 7-8 by addition of 50 percent NaOH solution and the solution of was saturated with solid NaCl. The precipitated product was taken up in 150 ml dichloromethane. The inorganic solids were removed from the aqueous phase by filtration and the filtrate was extracted with dichloromethane (4×50 mL). The combined extracts were dried over sodium sulfate and evaporated to yield 15.6 g (38 percent yield).

Preparation of 2-Fluoro-6-pyrazol-1-yl-pyridine

Sodium hydride / 60 percent oil dispersion (0.80 g, 20 mmol) was added over 5 minutes to a solution of pyrazole (1.4 g, 20 mmol) in DMF (20 mL) and THF (6 mL). After 10 minutes, 2,6-difluoropyridine (1.9 mL, 21 mmol) was added in one portion. After stirring for 20 h, the reaction was diluted with water (250 mL) and extracted with ether (5×50 mL). The organics were combined, washed with water (3×50 mL), brine (50 mL) and dried ($Na_2SO_4$). Filtration and removal of solvent left a gold oil that was purified by reverse phase liquid chromatography, affording product as a colorless oil, 2.0 g, 12.3 mmol, 61 percent yield.

Preparation of 3-(t-Butyl)-[1,2,4]oxadiazol-5-yl)-6-methanesulfonylpyridine 3-t-Butyl-5-(6-methylthio-2-pyridinyl)-1,2,4-oxadiazole was dissolved with stirring in $CH_2Cl_2$ (50 mL) and mCPBA (2.66 g, assumed 60 percent) added, stirred overnight at room temperature. 10 percent sodium carbonate solution (50 mL) was added and stirred for 30 min. After separation, the organic extract was washed twice with 2M sodium hydroxide solution (50 mL), dried over $Na_2SO_4$, and the solvent evaporated under reduced pressure to give 1.1 g of 3-t-butyl-5-(6-methylsulfonyl-2-pyridinyl)-1,2,4-oxadiazole as a white solid, m.p. 165-167° C.

Preparation of 3-(t-Butyl[1.2,4]oxadiazol-5-yl)-6-methanesulfanylpyridine 3-t-Butyl-5-(6-chloro-2-pyridinyl)-1,2,4-oxadiazole (1.2 g) was stirred in t-butanol (15 mL) and sodium methanethiolate (0.31 g) was added and stirred at 50° C. overnight. Additional sodium methanethiolate (0.10 g) was added and the reaction was heated under reflux for 3 h. Upon cooling, the mixture was poured onto ice, extracted with a mixture of 50 percent EtOAc/hexane. The organic extracts were washed with water and brine, dried over $Na_2SO_4$, filtered, evaporated under reduced pressure to give a clear oil which crystallized on standing to 1.23 g of 3-t-butyl-5-(6-methylthio-2-pyridinyl)-1,2,4-oxadiazole as a white solid, m.p. 62-64° C.

Preparation of 3-(t-Butyl)-[1,2,4]oxadiazol-5-yl)-6-chloropyridine t-Butylamidoxime (1.16 g ) was dissolved with stirring in toluene (60 mL) and triethylamine (2.0 g) added, followed by a solution of the 6-chloro-2-pyridinyl carbonyl chloride (1.76 g) in toluene (10 mL. The mixture was stirred overnight and then heated under Dean Stark conditions for 4 h, cooled, filtered, and evaporated to dryness. The residue was purified on silica gel by chromatography (1-10 percent EtOAc in Hexane) to give 3-t-butyl-5-(6-chloro-2-pyridinyl)-1,2,4-oxadiazole as a white solid: m.p. 103-104° C.

Preparation of 5-(tert-butyl)-3-(6-fluoropyridin-2-yl)-3H-[1,3,4]oxadiazol-2-one This was prepared using 2,6-difluoropyridine according to the method of Giacobbe, T. J. *J Heterocyclic Chem*. 1978,15, 1221.

Preparation of 5-Difluoromethoxy-3-methyl-2-methanesulfonylpyridine

Solid 3-chloroperbenzoic acid (60 percent, 18.1 g, 68.6 mmol) was added in portions over 1 hour to a chilled (6° C.) solution of 5-difluoromethoxy-3-methyl-2-methylsulfanylpyridine (6.4 g, 31.2 mmol) in methylene chloride (200 mL). The reaction was stirred overnight while warming to room temperature. Aqueous 1N sodium hydroxide (65 mL) was added in portions, raising the pH to ca. 6. Saturated aq. sodium bicarbonate (60 mL) was added, raising the pH of the aqueous phase to ca. 8. Aqueous 10 percent sodium sulfite was added, and after stirring for 10 minutes, the layers were separated. The aqueous layer was extracted with methylene chloride (50 mL) and the organic layers were combined, washed with brine, and dried (Na$_2$SO$_4$). Filtration and removal of solvent left a clear oil, 8 g, that was purified by chromatography on silica, eluting with 1.5 vol percent acetonitrile in methylene chloride to give product, 6.3 g, 26.6 mmol, 85 percent yield.

Preparation of 5-Difluoromethoxy-3-methyl-2-methylsulfanylpyridine

Solid sodium hydroxide (9.3 g, 232 mmol) were added in one portion to a stirred solution of 5-methyl-6-methylsulfanylpyridine-3-ol (7.2 g, 46.4 mmol) in 1,4-dioxane (75 mL) and water (25 mL) causing an exotherm to 50° C. Chlorodifluoromethane (13 g, 150 mmol) was then rapidly bubbled into the reaction over 9 minutes, causing a gradual exotherm to 75° C. After the reaction had cooled to room temperature, it was diluted with ether (100 mL) and water (100 mL) and the layers separated. The organic phase was extracted with water (6×100 mL), brine and dried (Na$_2$SO$_4$). Filtration and removal of solvent left a brown oil, 8.3 g, that was purified by chromatography on silica, eluting with 1:1 methylene chloride/hexanes to give product, as an orange liquid, 5.8 g, 28.3 mmol, 61 percent yield.

Preparation of 5-methyl-6-methylsulfanylpyridine-3-ol

A slurry of 5-amino-3-methyl-2-methylsulfanylpyridine (20.3 g, 132 mmol) in 20 wt percent aqueous sulfuric acid (170 mL) was cooled to −2° C. via an ice/salt water bath. A solution of sodium nitrite (9.1 g, 132 mmol) in water (30 mL) was added dropwise, maintaining the internal temperature at or below 1° C. After stirring for an additional 20 minutes, the reaction mixture was cautiously poured in portions into a rapidly stirred, hot (100° C.) solution of 20 wt. percent aqueous sulfuric acid (330 mL). Stirring was continued for 10 minutes, then the mixture was allowed to cool to room temperature. The reaction was washed with methylene chloride (3×200 mL), then the pH of aqueous layer was raised to 4-5 (in the cold) with 50 wt percent aq. sodium hydroxide (ca. 160 mL). A precipitate consisting of both a white solid and a reddish brown oil had formed. Additional 20 wt percent aq. sodium hydroxide was added, raising the pH to 6 and resulting in more precipitate/oil formation. The mixture was cooled and filtered, collecting the white solid, while the majority of colored oil remained in the mother liquor. The collected solid was taken up in 5 percent aq. sodium hydroxide (300 mL) and washed with ether (2×100 mL) to remove impurities and unreacted starting material. The aqueous portion was then treated with activated charcoal, filtered through celite, and the pH adjusted to 5-6 with glacial acetic acid. The precipitate was collected by filtration and dried in vacuo affording an off-white powder, 14 g, 90 mmol, 68 percent yield.

Preparation of 5-amino-3-methyl-2-methylsulfanylpyridine

3-Methyl-2-methanesulfanyl-5-nitropyridine (25.0 g, 136 mmol) was added in 5 g increments to a mechanically stirred, heated (70° C.) slurry of iron powder (27 g, 483 mmol, 3.5 equiv) and ammonium chloride (10.0 g, 187 mmol) in water (250 mL). After 45 minutes, the hot reaction mixture was filtered through a bed of celite. The celite bed was rinsed well with water, then with methylene chloride until no more gold color was evident. After cooling to room temperature, the layers were separated and the aqueous phase extracted with methylene chloride (2×250 mL). The organic portions were combined, reduced in volume to ca. one liter, washed with brine and dried (Na$_2$SO$_4$). Filtration and removal of solvent left a brown liquid which slowly solidified, 20.4 g, 132 mmol, 97 percent yield.

Compounds 1-133 are listed below in TABLE I.

TABLE I

| Compound Number | MOLSTRUCTURE | m/z |
|---|---|---|
| 1 | | 451 |
| 2 | | 461 |

TABLE I-continued

| Compound Number | MOLSTRUCTURE | m/z |
|---|---|---|
| 3 | | 428 |
| 4 | | 408 |
| 5 | | 308 |
| 6 | | 482 |
| 7 | | 308 |
| 8 | | 460 |

TABLE I-continued

| Compound Number | MOLSTRUCTURE | m/z |
|---|---|---|
| 9 | | 484 |
| 10 | | 433 |
| 11 | | 427 |
| 12 | | 450 |
| 13 | | 407 |
| 14 | | 410 |

TABLE I-continued

| Compound Number | MOLSTRUCTURE | m/z |
|---|---|---|
| 15 | | 444 |
| 16 | | 467 |
| 17 | | 383 |
| 18 | | 382 |
| 19 | | 398 |
| 20 | | 440 |

TABLE I-continued
| Compound Number | MOLSTRUCTURE | m/z |
|---|---|---|
| 21 | 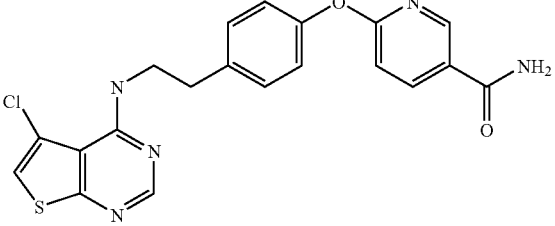 | 425 |
| 22 | 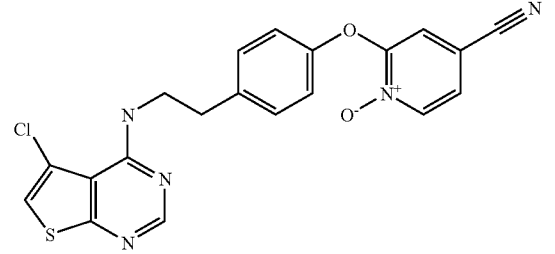 | 423 |
| 23 | 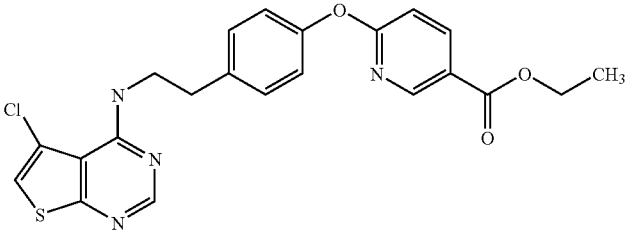 | 454 |
| 24 | 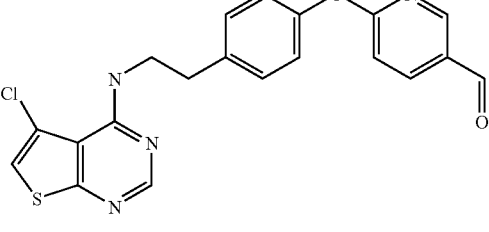 | 410 |
| 25 | 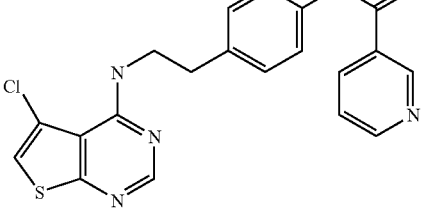 | 383 |
| 26 | 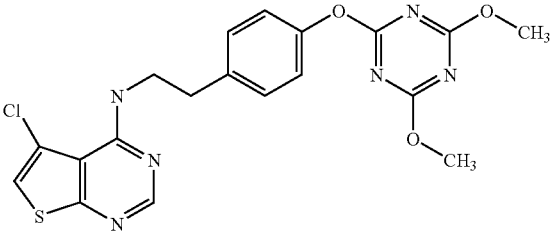 | 445 |

TABLE I-continued

| Compound Number | MOLSTRUCTURE | m/z |
|---|---|---|
| 27 | | 452 |
| 28 | | 407 |
| 29 | | 425 |
| 30 | | 425 |
| 31 | | 451 |

TABLE I-continued

| Compound Number | MOLSTRUCTURE | m/z |
|---|---|---|
| 32 | | 407 |
| 33 | | 467 |
| 34 | | 439 |
| 35 | | 460 |
| 36 | | 400 |
| 37 | | 416 |

TABLE I-continued

| Compound Number | MOLSTRUCTURE | m/z |
|---|---|---|
| 38 | | 383 |
| 39 | | 424 |
| 40 | | 408 |
| 41 | | 408 |
| 42 | | 474 |
| 43 | | 508 |

TABLE I-continued

| Compound Number | MOLSTRUCTURE | m/z |
|---|---|---|
| 44 | | 481 |
| 45 | | 418 |
| 46 | | 430 |
| 47 | | 451 |
| 48 | | 430 |
| 49 | | 354 |

TABLE I-continued

| Compound Number | MOLSTRUCTURE | m/z |
|---|---|---|
| 50 | | 474 |
| 51 | | 494 |
| 52 | | 445 |
| 53 | | 373 |
| 54 | | 439 |
| 55 | | 391 |

TABLE I-continued

| Compound Number | MOLSTRUCTURE | m/z |
|---|---|---|
| 56 | | 459 |
| 57 | | 561 |
| 58 | | 441 |
| 59 | | 441 |
| 60 | | 413 |

TABLE I-continued

| Compound Number | MOLSTRUCTURE | m/z |
|---|---|---|
| 61 | | 486 |
| 62 | | 484 |
| 63 | | 480 |
| 64 | | 484 |
| 65 | | 450 |

TABLE I-continued

| Compound Number | MOLSTRUCTURE | m/z |
|---|---|---|
| 66 | | 438 |
| 67 | | 450 |
| 68 | | 473 |
| 69 | | 450 |
| 70 | | 462 |

TABLE I-continued

| Compound Number | MOLSTRUCTURE | m/z |
|---|---|---|
| 71 | | 441 |
| 72 | | 456 |
| 73 | | 450 |
| 74 | | 407 |
| 75 | | 518 |

TABLE I-continued
| Compound Number | MOLSTRUCTURE | m/z |
|---|---|---|
| 76 | 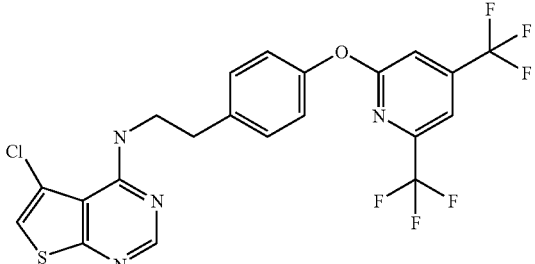 | 518 |
| 77 | 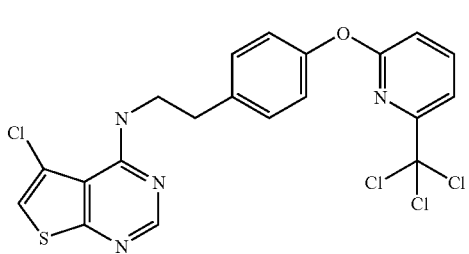 | 498 |
| 78 | 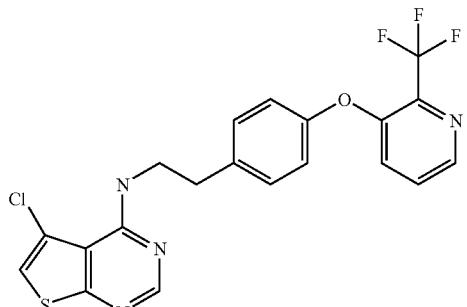 | 450 |
| 79 | 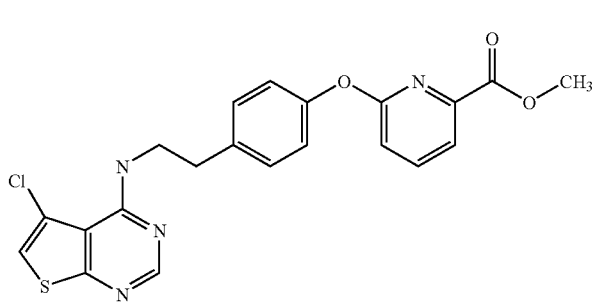 | 440 |
| 80 | 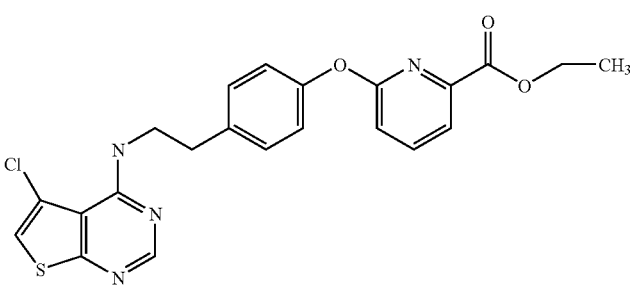 | 454 |

TABLE I-continued

| Compound Number | MOLSTRUCTURE | m/z |
|---|---|---|
| 81 | | 437 |
| 82 | | 425 |
| 83 | | 427 |
| 84 | | 337 |
| 85 | | 396 |
| 86 | | 440 |

TABLE I-continued

| Compound Number | MOLSTRUCTURE | m/z |
| --- | --- | --- |
| 87 | | 490 |
| 88 | | 494 |
| 89 | | 448 |
| 90 | | 465 |
| 91 | | 460 |

TABLE I-continued

| Compound Number | MOLSTRUCTURE | m/z |
|---|---|---|
| 92 | | 478 |
| 93 | | 496 |
| 94 | | 532 |
| 95 | | 460 |
| 96 | | 506 |

TABLE I-continued

| Compound Number | MOLSTRUCTURE | m/z |
|---|---|---|
| 97 | | 421 |
| 98 | | 494 |
| 99 | | 443 |
| 100 | | 424 |
| 101 | | 407 |
| 102 | | 496 |

TABLE I-continued

| Compound Number | MOLSTRUCTURE | m/z |
|---|---|---|
| 103 | | 461 |
| 104 | | 382 |
| 105 | | 453 |
| 106 | | 502 |
| 107 | | 441 |
| 108 | | 472 |

TABLE I-continued

| Compound Number | MOLSTRUCTURE | m/z |
|---|---|---|
| 109 | | 445 |
| 110 | | 454 |
| 111 | | 479 |
| 112 | | 469 |
| 113 | | 498 |
| 114 | | 404 |

TABLE I-continued
| Compound Number | MOLSTRUCTURE | m/z |
|---|---|---|
| 115 | 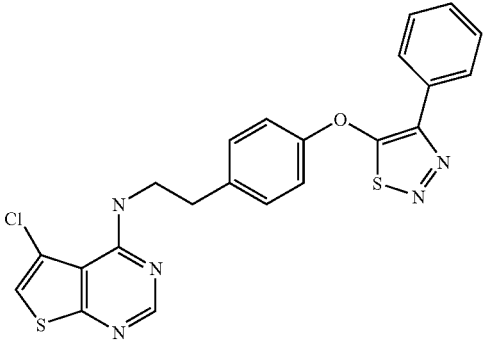 | 466 |
| 116 | 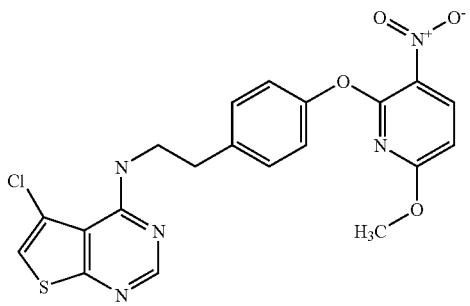 | 456 |
| 117 | 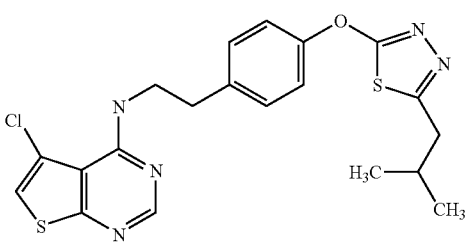 | 446 |
| 118 | 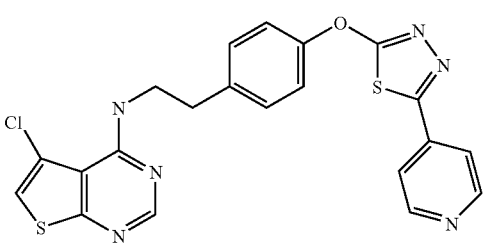 | 467 |
| 119 | 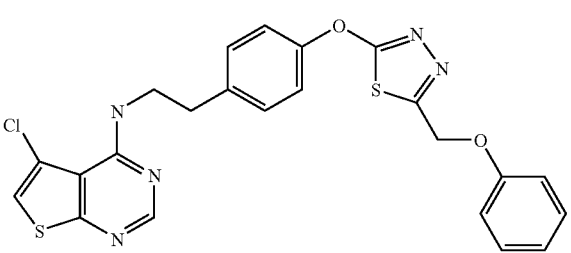 | 496 |

TABLE I-continued

| Compound Number | MOLSTRUCTURE | m/z |
| --- | --- | --- |
| 120 | | 424 |
| 121 | | 451 |
| 122 | | 420 |
| 123 | | 466 |
| 124 | | 480 |
| 125 | | 408 |

TABLE I-continued
| Compound Number | MOLSTRUCTURE | m/z |
|---|---|---|
| 126 | 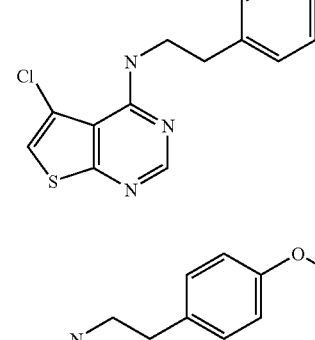 | 450 |
| 127 | | 480 |
| 128 | 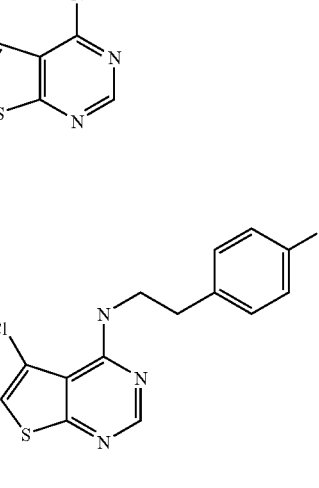 | 451 |
| 129 | 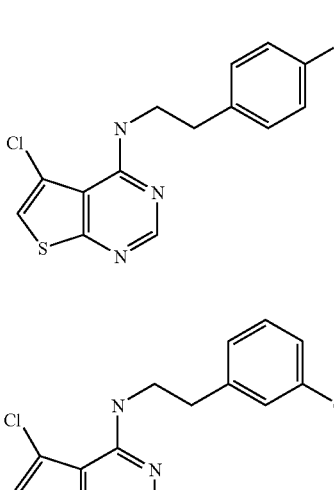 | 436 |
| 130 | 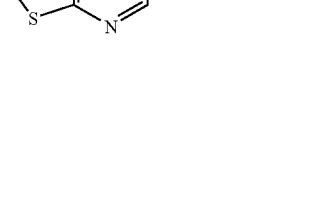 | 441 |

TABLE I-continued

| Compound Number | MOLSTRUCTURE | m/z |
|---|---|---|
| 131 | 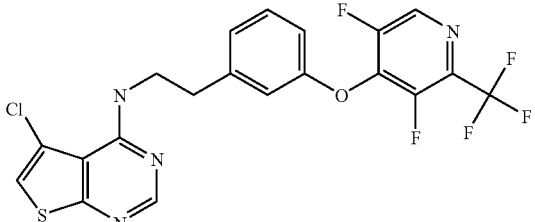 | 486 |
| 132 | 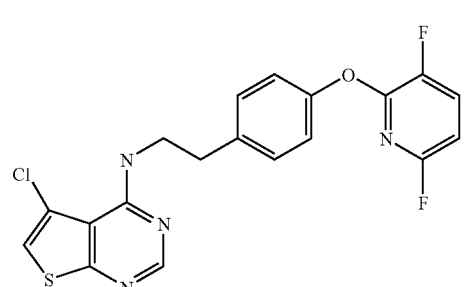 | 418 |
| 133 | 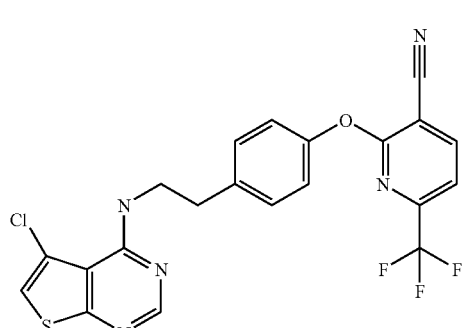 | 475 |

The compounds of the present invention have been found to have significant fungicidal effect particularly for agricultural use. Many of the compounds are particularly effective for use with agricultural crops and horticultural plants.

In particular, the compounds effectively control a variety of undesirable fungi that infect useful plant crops. Activity has been demonstrated for a variety of fungi, including for example the following representative fungi species: Anthracnose of Cucumber (*Collatotrichum lagenarium* - COLLLA); Spot Blotch of Wheat (Cochliobolus sativus-COCHSA), Rice blast (Magnaporthe grisea-PYRIOR), Late Blight of Tomato and Potato (*Phytophthora infestans* - PHYTIN); Brown Rust of Wheat (*Puccinia recondita tritici* - PUCCRT); Powdery Mildew of Wheat (*Erysiphe graminis* - ERYSGT); Powdery Mildew of Cucumber (*Erysiphe cichoracearum* - ERYSCI); Leaf Blotch of Wheat (*Septoria tritici* - SEPTTR); and Glume Blotch of Wheat (*Septoria nodorum* - LEPTNO).

It will be understood by those in the art that the efficacy of the compounds against the foregoing fungi establishes the general utility of the compounds as fungicides.

Biological Testing

The activity of the compounds as effective fungicides was determined by applying the compounds to plants and observing control of fungal disease. The compounds were formulated at 200 ppm in 10 vol.% acetone plus 90 vol.% Triton X water (deionized water 99.99 wt% +0.01 wt% Triton X100), giving a "formulated test compound." In a few cases, compounds were formulated at 100, 75 or 8.3 ppm rather than 200 ppm in 10 vol. % acetone plus 90 vol. % Triton X water (deionized water 99.99 wt. % +0.01 wt. % Triton X100), giving a 'formulated test compound'. The compounds were tested for ability to control plant diseases in a 1-day protectant test (1DP) or a 2-day curative test (2DC). Formulated test compounds were applied to plants using a turn table sprayer fitted with two opposing air atomization nozzles which delivered approximately 1500 L/ha of spray volume. Plants were inoculated with spores of the fungus the next day (1DP), then incubated in an environment conducive to disease development. In a few cases, the compounds were tested for ability to control plant disease in a two-day curative test. Plants were inoculated with spores of the fungus two days prior to compound application, and incubated in an environment conducive to disease development both before and after compound application (2DC). For all types of tests, disease severity was evaluated 4 to 28 days later, depending on the speed of disease development.

The following experiments were performed in the laboratory to determine the fungicidal efficacy of the compounds of the invention.

Leaf Rust of Wheat (causal agent *Puccinia recondita tritici=Puccinia triticina*; Bayer code PUCCRT): Wheat plants (variety Yuma) were grown from seed in a soil-less peat-based potting mixture (Metromix) until the seedlings had a fully expanded first leaf. Each pot contained 3-8 seedlings. These plants were sprayed until wet with the formulated test compounds. On the following day, the leaves were inoculated with an aqueous spore suspension of *Puccinia recondita tritici* and the plants were kept in high humidity overnight to permit spores to germinate and infect the leaf. The plants were then transferred to a greenhouse until disease developed on untreated control plants.

Cucumber Anthracnose (causal agent *Colletotricum lagenarium*; Bayer code COLLLA): Cucumber plants (variety Bush Champion) were grown from seed in a soil-less peat-based potting mixture (Metromix) until the first true leaf was 20-80% expanded. Each pot contained 1 seedling. These plants were sprayed until wet with the formulated test compound. On the following day, the leaves were inoculated with an aqueous spore suspension of *Colletotricum lagenarium* and the plants were kept in high humidity for one day to permit spores to germinate and infect the leaf. The plants were then transferred to a growth chamber until disease developed on untreated control plants.

Cucumber Powdery Mildew (causal agent *Erysiphe cichoracaerum*; Bayer code ERYSCI): Cucumber plants (variety Bush Champion) were grown from seed in a soil-less peat-based potting mixture (Metromix) until the first true leaf was 20-80% expanded. Each pot contained 1 seedling. These plants were sprayed until wet with the formulated test compound. On the following day, the leaves were inoculated with an aqueous spore suspension of powdery mildew spores (approximately 50,000 spores per milliliter). The plants were then incubated in a greenhouse until disease developed on untreated control plants.

Glume Blotch of Wheat (causal agent *Leptosphaeria nodorum=Stagnospora nodorum*; Bayer code LEPTNO): Wheat plants (variety Yuma) were grown from seed in a 50% pasteurized soil/50% soil-less mix until the seedlings had a fully expanded first leaf. Each pot contained 3-20 seedlings. These plants were sprayed until wet with the formulated test compound. On the following day, (or two days before application for a two-day curative test), the leaves were inoculated with an aqueous spore suspension of *Leptosphaeria nodorum* and the plants were kept in high humidity (one day in a dark dew chamber followed by four to seven days in a lighted dew chamber) to permit spores to germinate and infect the leaf. The plants were then transferred to a greenhouse until disease developed on untreated control plants.

Tomato Late Blight (causal agent *Phytophthora infestans*; Bayer code PHYTIN): Tomato plants (variety Outdoor Girl or Rutgers) were grown from seed in a soil-less peat-based potting mixture (Metromix) until the second true leaf was 30-100% expanded. Each pot contained 1 seedling. These plants were sprayed until wet with the formulated test compound. On the following day, the leaves were inoculated with an aqueous suspension of *Phytophthora infestans* sporangia and zoospores, and the plants were kept in high humidity for one day to permit sporangia and zoospores to germinate and infect the leaf. The plants were then transferred to a growth chamber until disease developed on untreated control plants.

Rice Blast (causal agent *Magnaporthe grisea=Pyricularia oryzae*; Bayer code PYRIOR): Rice plants (variety M202) were grown from seed in a soil-less peat-based potting mixture (Metromix) until the seedlings had a partly to fully expanded second leaf. Each pot contained 5-20 seedlings. These plants were sprayed until wet with the formulated test compound. On the following day, the leaves were inoculated with an aqueous spore suspension of *Pyricularia oryzae* and the plants were kept in high humidity overnight to permit spores to germinate and infect the leaf. The plants were then transferred to a growth chamber at 22-24 C. until disease developed on untreated control plants.

Speckled Leaf Blotch of Wheat (*Mycosphaerella graminicola=Septoria tritici*; Bayer code SEPTTR): Wheat plants (variety Monon or Yuma) were grown from seed in a greenhouse in 50% pasteurized soil/50% soil-less mix until the first true leaf was fully expanded, with 3-8 seedlings per pot. These plants were sprayed until wet with the formulated test compound. On the following day, (or two days before application for a two-day curative test), the leaves were inoculated with an aqueous spore suspension of *Septoria tritici* and the plants were kept in high humidity (one day in a dark dew chamber followed by four to seven days in a lighted dew chamber) to permit spores to germinate and infect the leaf. The plants were then transferred to a greenhouse until disease developed on untreated control plants.

The following table presents the activity of typical compounds of the present invention when evaluated in these experiments. The effectiveness of the test compounds in controlling disease was determined by assessing the severity of disease on treated plants, then converting the severity to percent control based on the level of disease on untreated, inoculated plants.

TABLE II: Activity of compounds as fungicides. Data are the level at which the given disease was controlled when the given compound was applied to the foliage of the plant at 200 ppm. In a few cases (noted in the table) the compound was applied to the plant at 100 ppm, 75 ppm or 8.3 ppm. The plant was inoculated with the fungus one day after treatment. In a few cases (noted in the table) the plant was inoculated with the fungus two days before treatment.

TABLE I

| Compound | COLLLA | ERYSCI | LEPTNO | PHYTIN | PUCCRT | PYRIOR | SEPTTR |
|---|---|---|---|---|---|---|---|
| 1 | * | ** | ** | * | *** | *** | ** |
| 2 | * | * | * | * | *** | ** | NT |
| 3 | ** | ** | ** | *** | *** | *** | ** |
| 4 | *** | *** | *** | *** | *** | *** | ** |
| 5 | ** | ** | *** | *** | *** | *** | ** |
| 6 | ** | *** | * | ** | *** | *** | ** |
| 7 | ** | *** | *** | * | *** | ** | ** |
| 8 | ** | ** | * | * | *** | ** | ** |
| 9 | ** | * | * | * | *** | ** | * |
| 10 | ** | *** | * | * | *** | *** | * |
| 11 | NT | NT | *** a | NT | *** a | NT | * |
| 12 | ** | *** | *** | ** | *** | *** | ** |
| 13 | ** | *** | *** | ** | *** | *** | ** |
| 14 | * | * | ** | * | *** | *** | * |
| 15 | * | * | ** | * | *** | *** | * |

TABLE I-continued

| Compound | COLLLA | ERYSCI | LEPTNO | PHYTIN | PUCCRT | PYRIOR | SEPTTR |
|---|---|---|---|---|---|---|---|
| 16 | * | ** | * | *** | *** | *** | *** |
| 17 | * | ** | ** | *** | *** | *** | ** |
| 18 | * | *** | * | *** | *** | *** | ** |
| 19 | * | ** | * | *** | *** | *** | ** |
| 20 | * | * | * | * | *** | * | NT |
| 21 | * | * | * | * | *** | * | * |
| 22 | ** | ** | ** | ** | *** | *** | * |
| 23 | * | * | * | ** | *** | ** | * |
| 24 | ** | * | * | ** | *** | *** | ** |
| 25 | * | * | ** | * | *** | ** | * |
| 26 | * | * | * | * | *** | ** | * |
| 27 | ** | *** | * | ** | *** | *** | ** |
| 28 | ** | * | ** | * | *** | ** | ** |
| 29 | ** | * | * | * | *** | ** | ** |
| 30 | *** | ** | * | ** | *** | *** | ** |
| 31 | * | * | * | * | *** | ** | * |
| 32 | ** | *** | * | ** | *** | *** | ** |
| 33 | ** | * | * | ** | *** | *** | * |
| 34 | *** | *** | * | * | *** | *** | ** |
| 35 | ** | *** | ** | ** | *** | *** | ** |
| 36 | ** | *** | * | * | *** | *** | ** |
| 37 | *** | *** | * | * | *** | *** | ** |
| 38 | ** | ** | * | ** | *** | ** | ** |
| 39 | * | ** | * | *** | *** | *** | * |
| 40 | * | ** | * | *** | *** | *** | * |
| 41 | * | ** | * | *** | *** | *** | * |
| 42 | * | * | ** | * | * | *** | *** |
| 43 | ** | *** | *** | * | *** | *** | *** |
| 44 | * | ** | *** | ** | *** | *** | *** |
| 45 | * | * | * | * | *** | ** | ** |
| 46 | * | * | * | * | *** | ** | ** |
| 47 | * a | *** a | *** b | * a | *** c | *** c | ** |
| 48 | ** | *** | * | *** | *** | *** | ** |
| 49 | ** | *** | ** | *** | *** | *** | ** |
| 50 | ** | * | ** | *** | *** | *** | ** |
| 51 | * | * | * | * | *** | *** | ** |
| 52 | ** | ** | ** | * | *** | *** | *** |
| 53 | *** | ** | ** | *** | *** | *** | ** |
| 54 | *** | ** | ** | *** | *** | *** | * |
| 55 | *** | ** | * | ** | *** | * | ** |
| 56 | ** | ** | * | *** | *** | *** | ** |
| 57 | ** | * | * | * | *** | *** | * |
| 58 | * | * | ** | * | *** | *** | ** |
| 59 | *** | ** | * | * | *** | *** | * |
| 60 | *** | *** | * | *** | *** | *** | ** |
| 61 | *** | *** | ** | * | *** | *** | *** |
| 62 | *** | ** | * | * | *** | *** | ** |
| 63 | ** | *** | * | ** | *** | *** | ** |
| 64 | ** | *** | * | * | *** | *** | *** |
| 65 | *** | ** | ** | *** | *** | *** | *** |
| 66 | * | * | * | * | *** | ** | ** |
| 67 | * | ** | ** | ** | *** | *** | *** |
| 68 | * | * | * | ** | *** | *** | * |
| 69 | * | ** | * | * | *** | *** | ** |
| 70 | *** | * | *** | ** | *** | *** | *** |
| 71 | *** | ** | *** | * | *** | *** | *** |
| 72 | * | *** | ** | * | *** | *** | ** |
| 73 | * | ** | ** | *** | *** | *** | ** |
| 74 | *** | * | *** | ** | *** | *** | ** |
| 75 | *** | *** | *** | * | *** | *** | ** |
| 76 | ** | * | ** | * | *** | *** | * |
| 77 | * | * | *** | * | *** | *** | * |
| 78 | ** | *** | *** | ** | *** | *** | ** |
| 79 | * | * | * | *** | *** | *** | * |
| 80 | * | * | * | *** | *** | *** | * |
| 81 | ** | ** | *** | * | *** | *** | ** |
| 82 | NT | NT | ** b | NT | *** c | *** c | ** |
| 83 | NT | NT | ** b | NT | *** c | *** c | ** |
| 84 | NT | NT | ** b | NT | *** c | *** c | ** |
| 85 | ** | *** | *** | *** | *** | *** | *** |
| 86 | * | ** | ** | *** | *** | ** | *** |
| 87 | * | *** | ** | ** | *** | *** | ** |
| 88 | ** | *** | ** | * | *** | *** | ** |
| 89 | * | *** | *** | * | *** | *** | ** |
| 90 | NT | NT | * b | NT | * c | ** c | ** |
| 91 | * | ** | *** | *** | *** | *** | * |
| 92 | NT | NT | * b | NT | *** c | *** c | ** |

TABLE I-continued

| Compound | COLLLA | ERYSCI | LEPTNO | PHYTIN | PUCCRT | PYRIOR | SEPTTR |
|---|---|---|---|---|---|---|---|
| 93 | NT | NT | * b | NT | *** c | *** c | ** |
| 94 | ** | ** | * | * | *** | *** | * |
| 95 | ** | * | *** | *** | *** | *** | ** |
| 96 | NT | NT | ** b | NT | *** c | ** c | ** |
| 97 | ** | * | *** | *** | *** | *** | ** |
| 98 | NT | NT | * b | NT | * c | * c | ** |
| 99 | ** | * | * | ** | *** | *** | * |
| 100 | NT | NT | * b | NT | *** c | *** c | NT |
| 101 | * | * | ** | * | *** | *** | ** |
| 102 | NT | NT | * b | NT | * c | ** c | * |
| 103 | ** | * | ** | * | ** | ** | * |
| 104 | ** | * | * | * | *** | *** | ** |
| 105 | * | * | * | * | ** | *** | * |
| 106 | * | * | * | * | *** | *** | ** |
| 107 | * | * | * | *** | *** | *** | ** |
| 108 | * | * | * | * | * | ** | ** |
| 109 | NT | NT | ** b | NT | *** c | *** c | ** |
| 110 | ** | *** | ** b | * | *** | *** | ** |
| 111 | NT | NT | * b | NT | ** c | *** c | ** |
| 112 | ** | * | * | ** | *** | *** | * |
| 113 | NT | NT | * b | NT | *** c | *** c | * |
| 114 | ** | *** | ** | *** | *** | *** | ** |
| 115 | NT | NT | ** b | NT | *** c | ** c | ** |
| 116 | NT | NT | * b | NT | *** c | * c | * |
| 117 | NT | NT | * b | NT | *** c | *** c | * |
| 118 | NT | NT | * b | NT | *** c | *** c | * |
| 119 | NT | NT | * b | NT | *** c | *** c | * |
| 120 | * | * | * b | ** | *** | ** c | * |
| 121 | NT | NT | * b | NT | *** c | *** c | * |
| 122 | ** | *** | * b | ** | *** | *** c | ** |
| 123 | NT | NT | NT | NT | NT | NT | NT |
| 124 | ** | *** | * b | ** | *** | *** c | * |
| 125 | * | ** | * b | ** | *** | *** c | ** |
| 126 | NT | NT | ** b | NT | *** c | NT | *** |
| 127 | NT | NT | *** b | NT | *** c | NT | ** |
| 128 | NT | NT | NT | NT | *** c | *** c | NT |
| 129 | NT | NT | ** b | NT | *** | *** | *** |
| 130 | * | * | NT | *** | *** | *** | * |
| 131 | NT | NT | NT | NT | ** c | NT | NT |
| 132 | NT | NT | NT | NT | *** c | *** c | NT |
| 133 | NT | NT | NT | NT | * c | NT | NT |

Activity at 200 ppm (except SEPTTR which was tested at 75 ppm)
* = 0–49 percent control;
** = 50–79 percent control;
*** = 80–100 percent control
a indicates that compound was tested at 100 ppm
b indicates that compound was tested at 75 ppm
c indicates that compound was tested at 8.3 ppm
NT indicates not tested

We claim:

1. A compound having the formula (I):

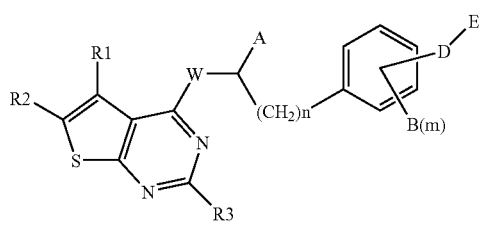

wherein each R1, R2 and R3 is independently selected from the group consisting of H and halogen;
A is selected from the group consisting of H and alkyl;
W is selected from the group consisting of NH and O;
D is selected from O, NH and S;
E is (—C(O)—)$_p$—R', wherein p is 0 or 1 and R' is selected from the group consisting of optionally substituted rings selected from phenyl, furanyl, pyridinyl, pyridinyl-N-oxide, pyrimidinyl, pyridazinyl, pyrazinyl, thiazolyl, triazinyl, thiadiazolyl, oxazolyl, isoxazolyl, thienopyrimidinyl, and pyrimidine fused with an aromatic or heteroaromatic ring selected from benzene, oxazole, isoxazole, furan, thiazole, pyrimidine, pyridine, pyrrole, pyrazine;
each ring being optionally substituted with one or more substituents selected from the group consisting of alkyl, alkenyl, alkynyl, halogen, haloalkyl, alkoxy, haloalkoxy, nitro, cyano, alkylsulfonyl, alkylsulfoxide, alkylthio, alkoxyiminoalkyl, alkylcarbonyl, alkoxycarbonyl, aminocarbonyl, hydroxycarbonyl, phenylcarbonyl, formyl, hydrazidocarbonyl, amidoamino, pyrazolyl, triazolonyl, oxadiazolyl, phenyl, pyridinyl, and phenoxyalkyl;
B is selected from the group consisting of halogen, alkyl, haloalkyl, alkoxy and haloalkoxy;
n is an integer from 0 to 3; and
m is an integer from 0 to 4 with the proviso that: when D is O or S and R' is phenyl, then R' is not further substituted with halogen or haloalkyl, and when D is O and R' is thienopyrimidinyl the R' is not further substituted with alkyl.

2. The compound of claim 1 wherein

R1 is halogen;

R2 and R3 are each H;

A is H;

W is selected from the group consisting of NH and O;

D is O;

E wherein p is 0 and R' selected from the group consisting of optionally substituted rings selected from pyridine, pyridine-N-oxide, pyrimidine, thiazole, and thienopyrimidine, optionally substituted with one or more groups selected from the group consisting of alkyl, haloalkyl, alkoxy, haloalkoxy, alkylsulfonyl, halogen, alkylcarbonyl, alkoxycarbonyl, aminocarbonyl, hydroxycarbonyl, formyl, hydrazidocarbonyl, alkoxyiminoalkyl, nitro, and cyano; and n is 1 and m is 0.

3. The compound of claim 1 wherein R1 is Cl and R2 is H.

4. The compound of claim 1 wherein W is NH, A is H and D is O.

5. The compound of claim 1 wherein p is 0.

6. A method for the control of fungal attack comprising applying to the soil, plant, roots, foliage, seed or locus of the fungus, or to a locus in which the infestation is to be prevented, a fungicidally effective amount of one or more of the compounds of claim 1.

7. A fungicidal composition for the control of fungal attack comprising a compound of claim 1 and a phytologically acceptable carrier material.

* * * * *